United States Patent [19]

Fields

[11] 4,069,271
[45] Jan. 17, 1978

[54] SILVER CATALYSTS

[75] Inventor: Ellis K. Fields, River Forest, Ill.

[73] Assignee: Standard Oil Company (Indiana), Chicago, Ill.

[21] Appl. No.: 706,531

[22] Filed: July 19, 1976

Related U.S. Application Data

[62] Division of Ser. No. 580,683, May 23, 1975, Pat. No. 4,005,049.

[51] Int. Cl.$^2$ ............................................. C07C 15/00
[52] U.S. Cl. ............................................... 260/669 R
[58] Field of Search .................................... 260/669 R

[56] References Cited

U.S. PATENT DOCUMENTS

| 2,040,782 | 5/1936 | Van Peski | 252/476 |
| 2,600,379 | 6/1952 | Doumani et al. | 260/669 R |

Primary Examiner—George Crasanakis
Assistant Examiner—Joseph A. Boska
Attorney, Agent, or Firm—William C. Clarke; Arthur G. Gilkes; William T. McClain

[57] ABSTRACT

Silver/transition metal catalysts are made by calcining the polysilver salt of a polycarboxylic acid and at least one transition metal salt of an organic polycarboxylic acid at temperatures from 200–500° C., and oxidizing the said calcined salts with oxygen at temperatures from 20–500° C.

3 Claims, No Drawings

SILVER CATALYSTS

This is a division of application Ser. No. 580,683, filed May 23, 1975, now U.S. Pat. No. 4,005,049.

BACKGROUND OF THE INVENTION

This invention relates to a new class of catalysts and to their production. More particularly, this invention relates to catalysts containing silver and transition metal moieties. These silver/transition metal catalysts are useful catalysts for isomerization, dehydrogenation, reduction and mild oxidations.

The use of silver alone as a catalyst, or promoted by certain other metals such as gold, copper, iron and manganese in the oxidation of ethylene to ethylene oxide, however, is well-known (P. G. Ashmore, *Catalysis and Inhibition of Chemical Reactions*, Butterworths, London, 242 (1963)) and has been taught by many examples in the prior art. For example, U.S. Pat. No. 2,605,239 teaches a silver-beryllium oxide catalyst for oxidizing ethylene to ethylene oxide. The patent teaches the source of the silver as being a reducible oxygen-containing compound such as the silver salt of a carboxylic acid, i.e., formic, acetic, propionic, oxalic, malonic and maleic acids, as well as others. Suitable promoters indicated include metals such as copper, aluminum, manganese, cobalt, iron, nickel, gold, cadmium and zinc. These may be incorporated by mixing or by coprecipitation.

It is also widely known that the addition of a second component to a material which acts as a catalyst as a single component may result in a combination having increased catalytic activity. It is equally widely known that the properties of a catalyst are determined by the total history of its preparation. Many catalysts consist of a major component of high area which is often referred to as the "support" with one or more components of smaller percentage. Even with high-area catalysts it is well-known that only a small percentage of the surface is active. The effect of the support on the other catalyst components and indeed the chemistry of surfaces and complexes is not well-understood. Accordingly, it is difficult to draw a distinction between the catalytic function of the "support" and the other catalyst components.

The use of silver in my invention in conjunction with transition metals of the Periodic Table results in unique catalysts whose specific catalytic activity can only be gauged by actual performance tests. The exact function of the silver which is both a support and catalyst component is not understood, i.e., the silver may be acting as the catalyst and the transition metals may be acting as "promoters." However, it is not feasible to differentiate in general between the two as the function between the two can vary for individual reactions.

It is, therefore, a general object of my invention to provide a new class of catalyst with high area silver supports which incorporate transition metals as co-catalysts and as promoters. A more particular object is to provide a practical and economic process for the manufacture of these catalysts. Another object of my invention is to provide catalysts with unique performance characteristics when employed in dehydrogenation, reduction and mild oxidation reactions. A further object of my invention is to provide improved silver catalysts and processes for using them in specific reactions which are of particular utility such as the direct vapor phase dehydrogenation of ethylbenzene to styrene. The nature of still other objects of my invention will be apparent from a consideration of the descriptive portion to follow.

It is my discovery that the above and other objects of the invention are attained by the silver/transition metal catalysts herein described.

The poly silver salts decarboxylate under the process conditions of my invention and form high polymers with the silver metal developing the desired high surface area as characterisitic property. It is important that polycarboxylic acid silver salts be used in my invention because, although the monocarboxylic acid silver salt decarboxylates under the process conditions of my invention, the monosilver salt residue forms dimers and low polymers with the silver metal in the form of a globule with low surface area and little catalyst activity. It is important that polycarboxylic acid transition metal salts be used to avoid interaction between salts that could lead to silver monocarboxylates. It is also preferable that the transition metal salts and silver salts be derived from the identical polycarboxylic acids rather than different polycarboxylic acids if the coprecipitation method of preparation is used. Use of other polycarboxylic acids in such circumstances can result in lessened catalytic activity because of different decomposition temperatures and the possible chemical interaction between the salts before the decomposition temperatures are reached. Coprecipitation might not occur with the two salts, preventing an ultimate intimate mixture of the two metals. If the metal salts are mixed intimately, as by milling together, the silver and transition metal salts may be derived from different polycarboxylic acids as, for example, disilver isophthalate and cobalt (II) trimesate.

The silver/transition metal catalyst prepared by the method of calcining silver and transition metal salts followed by oxidation at controlled temperatures quite surprisingly can act as catalysts for controlled mild oxidation, dehydrogenation and isomerization reactions at temperatures from 130 to 500° C. The lower limit of 130° C. is the lowest reasonable temperature consistent with a reasonable speed of reaction. The upper limit of 500° C. is the highest reasonable temperature consistent with physical characteristics of the reactants such as melting points, boiling points and decomposition temperatures.

For example, as will be shown in the illustrative examples, the silver/transition metal catalyst (where cobalt and nickel are transition metals) quite surprisingly dehydrogenates ethylbenzene to stryene with good to excellent selectivity. Generally the major constituent of catalysts for dehydrogenating ethylbenzene to styrene is iron oxide, although other oxides can be used such as those of magnesium, chromium, cesium, tungsten with, in some instances, oxides of aluminium, silicon and zinc. In these examples, conditions of reaction to dehydrogenate ethylbenzene to stryene are one atmosphere pressure with the temperature within the range from 220° to 300° C. The preferred temperature with silver/nickel catalyst is 260° C. With the silver/cobalt catalyst, the preferred temperature is 250° C.

For example, as will be shown in the illustrative examples, the silver/transition metal catalysts (where nickel, platinum or palladium comprise the transition metals), quite suprisingly can effect the oxidation of one methyl substituent on a benzene ring without affecting another alkyl or halogen substituent on the same ring. This system, which can be described as one of mild oxidation, can oxidize the individual isomeric xylenes to their corresponding m- and p-toluic acid, methyl benzaldehydes and methyl benzyl alcohols. This system of mild oxidation quite suprisingly attacks selectively the para-methyl substituents in preference to alkyl groups of more than one carbon in other positions and halogen substituents.

In the mild oxidation of meta- and paraxylenes using silver/nickel/platinum/or palladium catalyst, the conditions of reaction can be relatively mild. The range of temperatures can be from 130° C. at one atmosphere pressure to 200° C. at ten atmospheres pressure. The preferred conditions are within the range from 136° C. to 142° C. at 1 atmosphere pressure. In the case of the halogenated toluenes with one to three halogens attached to the ring, i.e., fluorine, chlorine and bromine, but not including iodine, the conditions of reaction are more stringent to give the correspondingly halogenated benzaldehydes and benzyl alcohols. A silver/palladium catalyst is used. The range of temperature can be from 140° C. at one atmosphere pressure to 200° C. at 1 to 5 atmospheres pressure. The preferred conditions are 155°–165° C. at 1 atmosphere.

In the mild oxidation of the methyl group of para-tert-butyltoluene to the corresponding acid, aldehyde, alcohol and ester, the range of temperature using a silver/palladium catalyst can be from 160° C. at 1 atmosphere to 250° C. at 7 atmospheres. Preferred conditions are from 188° to 191° C. at one atmosphere. A similar oxidation of 1-methylnaphthalene using silver/palladium catalyst can be from 200° C at 1 atmosphere to 300° C. at 7 atmospheres. Preferred conditions are from 241° C. to 245° C. at one atmosphere.

For example, the silver/transition metal catalyst (where palladium comprises the transition metal) quite suprisingly can effect the reduction of nitrobenzene to azobenzene with excellent selectivity. Prior art teaches the treatment of nitrobenzene with caustic soda in the presence of glucose, or with zinc dust and sodium hydroxide in methanol, or with iron and sodium hydroxide, or with hydrogen and bismuth as a catalyst. In this reduction, the range of temperature can be from 150° C. at 1 atmosphere to 250° C. at 7 atmospheres. The preferred conditon is the reflux temperature of nitrobenzene at 1 atmosphere, 211° C.

For example, the silver/transition metal catalyst (where vanadium comprises the transition metal) quite suprisingly can effect the isomerization of 1-pentene to the cis and trans forms of 2-pentene as well as to 2-methylbutene-2 at temperatures from 360° to 450° C. at one atmosphere. Preferred temperature is 400° C.

For example, the silver/transition metal catalyst (where vanadium comprises the transition metal) quite suprisingly can effect the oxidation of toluene to benzaldehyde with excellent selectivity at temperatures from 400° to 500° C. Preferred temperature is 450° C. at 1 atmosphere.

For example, the silver/transition metal catalyst (where palladium comprises the transition metal) quite suprisingly can effect the oxidative carboxymethylation of para-tert-butyltoluene to 2-methyl-5-tert-butylphenyl acetic acid with excellent selectivity. The range of temperatures is from 100° C. at 1 atmosphere to 150° C. at 7 atmospheres. Preferred temperature is 130° C. at 1 atmosphere.

DETAILED DESCRIPTION OF THE INVENTION

In general, the silver/transition metal catalysts of this invention are prepared by calcining silver and transition metal salts of di- and polycarboxylic acids at 200°–500° C. for 1 to 60 minutes in air, but preferably under inert gases such as nitrogen, argon, or helium, to produce carbon-like polymers containing silver and transition metals. The carbon-like polymers are allowed to burn off spontaneously by adding oxygen at controlled rates at 20°–500° C. The carbon-like polymers containing silver and transition metals can be cooled to ambient temperatures under nitrogen or hydrogen before the controlled combustion, then treated with oxygen or oxygen-containing mixtures. The organic material is then allowed to burn off by being heated to the temperature required for such oxidation, preferably the lowest temperature at which oxidation occurs to avoid unnecessary sintering of the silver/transition metal catalyst. Such temperatures usually will be from 100° to 200° C.

It is important that the calcining technique utilizing an inert gas be used because the calcining step forms a polymeric network of silver, transition metal and carbon-like polymer. Further oxidation removes the carbon-like polymer, leaving the silver as a support for the transition metal, both in a state of high surface area. Once the burn-off temperature has been determined, the cooling step to the ambient or below the burn-off temperature is not required. It is important to keep the burn-off temperature as low as possible to avoid local hot-spots and to avoid sintering with loss of surface area and consequent loss of catalytic activity. The use of an inert gas during calcining rather than oxygen aids in attaining these results. The polymeric network can be oxidized immediately after the formation of the network under the inert gas by cooling to the desired oxidation temperature, then introducing oxygen to allow combustion.

The use of hydrogen as a coolant during the cooling step to reduce the polymer temperature to below the burn-off temperature has been observed to be advantageous in that the burn-off temperature is lower than when the polymer is cooled with nitrogen. A concurrent increase in the activity of the resulting catalyst has been observed also.

For purposes of this invention, the term "silver salts of polycarboxylic acids" includes any silver salt of a carboxylic acid compound wherein the hydrogen of more than one carboxyl group attached to the aliphatic, alicyclic, aromatic, or heterocyclic moeity are replaced by silver metal radicals. For purposes of this invention, the transition metal salts are defined as being the metal salts of any polycarboxylic acid compound wherein the hydrogens of at least two carboxyl groups attached to the aliphatic, alicyclic, aromatic or heterocyclic moiety are replaced by transition metal radicals, such transition metals being selected from the group consisting of the metals of Groups IV-B, V-B, VI-B, VII-B, VIII and I-B of the Periodic Table including vanadium, chromium, manganese, iron, cobalt, nickel, copper, zirconium, molybdenum, ruthenium, rhodium, palladium, rhenium, platinum and gold. Particularly useful are the transition metal salts of cobalt, nickel, vanadium, palladium and platinum. Polyalkylbenzenes are defined as aromatic compounds with a plurality of alkyl groups attached to the benzene ring, said alkyl groups consisting of from one to eight carbon atoms.

For purposes of this invention, the term "aromatic compounds" is defined as including compounds characterized by at least one benzene ring, i.e., either the six-carbon ring of benzene or the condensed six-carbon rings of the other aromatic derivatives, such as naphthalene, phenanthrene, anthracene, etc. The term "heterocyclic compound" is defined as a compound containing a cyclic or ring of five or more atoms in the ring in which one or more of the atoms in the ring is an element other than carbon and can be oxygen, nitrogen and/or sulfur. The term "oxygen" is defined as including oxygen air, or other gaseous mixtures containing oxygen suitable for combustion.

Silver salts used in preparing the silver and transition metal catalysts of my invention have the formula $R(COOAg)_n$ where R is an aromatic or heterocyclic ring and $n$ is an integer from 2 to 8. Representative examples of the silver salts used in my invention are disilver terephthalate, disilver isophthalate, trisilver trimellitate, trisilver trimesate, trisilver hemimellitate, tetrasilver pyromellitate, tetrasilver mellophanate, pentasilver benzenepentacarboxylate, hexasilver mellitate, disilver salts of naphthalene 1,3-; 1,4-; 1,5-; 1,6-; 1/7-; 1,8-; 2,4-; 2,6-; and 2,7-dicarboxylic acids, tetrasilver 1,4,5,8-naphthalenetetracarboxylate, octasilver naphthaleneoctacarboxylate, disilver pyridine 2,4-, 2,5-, 2,6-, 3,5-, and 3,6-dicarboxylates, disilver thiophene-2,5-dicarboxylate, and the silver salts of di-, tri- and tetracarboxylic acids of anthracene, anthraquinone, phenanthrene, chrysene, perylene, quinoline, isoquinoline, phenanthridine, benzothiophene (thionaphthene) dibenzothiophene, benzofuran, and dibenzofuran.

Included among the silver salts used to prepare the silver/transition metal catalysts of my invention are those of the formula $(AgOOC)_n$-R-X-R'-$(COOAg)_m$ where R and R' are the same or different aryl or heterocyclic radicals, $n$ and $m$ are integers 1 to 4, and X is a divalent atom or radical such as —O—, —S—, —Se—, —NH—, —CH$_2$—, —CO—, —SO$_2$—, or —C≡C—. Examples of these silver salts are disilver diphenylether-4,4'-dicarboxylate, disilver methylenedibenzoate, disilver diphenylsulfone-4,4'-dicarboxylate, disilver benzophenone-4,4'-dicarboxylate, tetrasilver benzophenone-3,3', 4,4'-tetracarboxylate, disilver stilbene-4,4'-dicarboxylate, and disilver diphenylacetylene-4,4'-dicarboxylate.

Also included among the silver salts used to prepare the silver/transition metal catalyst of my invention are those of structure $AgOOC(CH_2)_nCOOAg$ and $AgOOC(CH=CH)_nCOOAg$ where $n$ is an integer from 1 to 6. Examples are disilver malonate, disilver succinate, disilver adipate, disilver fumarate, disilver 1,3-butadiene-1,4-dicarboxylate, and disilver 1,3,5-hexatriene-1,6-dicarboxylate.

The transition metal salts are derived from any of the polycarboxylic acids listed above in the silver salts. When the intimate mixture of silver/transition metal salt is prepared by coprecipitation, for example, by adding an aqueous solution of sodium isophthalate to an aqueous solution of silver nitrate and palladium nitrate to precipitate silver-palladium isophthalate, the silver and transition metal salts are, of course, derived from the identical acid. The silver salt and the transition salt can be prepared separately and mixed intimately as by milling together before the calcining process. In such preparations, the silver and transition metal salts can be derived from different polycarboxylic acids, for example, silver isophthalate and cobalt (II) trimesate. The atom ratio silver:transition metal can vary from 2:1 to 200:1. The preferred range is 5:1 to 50:1.

The new class of catalysts and the method of their production of my invention are silver/transition metal catalysts wherein the silver and transition metals are derived from polycarboxylic acid salts of these metals wherein the silver and transition metal salts are intimately mixed together and calcined at temperatures from 200°–500° C. under an inert gas. The resulting carbon-like polymers are allowed to burn-off spontaneously by adding oxygen, air or mixtures of nitrogen and oxygen at controlled rates at 20°–500° C. Alternatively, the carbon-like polymers containing silver and transition metals can be cooled to ambient temperatures under nitrogen or hydrogen, then treated with oxygen or oxygen-containing mixtures, such as air. The organic material is allowed to burn off, preferably at the lowest temperature at which oxidation occurs to avoid unnecessary sintering of the silver/transition metal catalyst. Such temperatures will usually be from 100° to 200° C.

There is a demand for new catalysts with specific catalytic activity such as the oxidation of one methyl substituent on a benzene ring without affecting another alkyl or halogen substituent on the same ring; the dehydrogenation of ethylbenzene to styrene, the reduction of nitrobenzene to azobenzene, among other catalytic reactions.

In order to facilite a clear understanding of the invention, i.e., the novel silver/transition metal catalyst and the method for making them, the following specific embodiments are described in detail. It should be understood, however, that the detailed expositions of the application of the invention, while indicating preferred embodiments, are given by way of illustration only since various changes and modifications within the spirit of the invention will become apparent to those skilled in the art from this detailed description.

EXAMPLE I

The coprecipitation technique of preparing the silver/transition metal catalysts is illustrated in the following.

9.27 Grams (0.1 mole) of nickelous hydroxide were stirred with 16.6 grams (0.1 mole) of isophthalic acid and 200 ml of water at 70° C. until all solids dissolved, approximately three hours. The clear solution was evaporated to dryness, yielding 22.3 grams of nickel isophthalate.

9.0 Grams of di-silver isophthalate and 1.0 gram of nickel isophthalate were mixed by milling together in a solids mill. Analysis by X-ray fluorescence and combustion of the silver-nickel isophthalate was C, 25.4%; H, 1.7%; Ag, 61.4%; Ni, 3.0%. The silver-nickel isophthalate was calcined at 400° C. in a Vycor tube under nitrogen flowing at 50 cc/min for five minutes to give an expanded carbon-like polymer matrix that analyzed: C, 9.6%; H, 0.6%; Ag, 77.0%; Ni, 4.9%. Analysis was by X-ray fluoresence and combustion. The matrix was allowed to cool under hydrogen to 20° C. Air was then admitted at 150 cc/min. the carbon-like matrix caught fire and the carbon burned off with no additional heating. The silver/nickel catalyst which remained analysed: C, 0.6%; H, 0.1%; Ag, 90.0%; Ni, 6.3%. Analysis was by X-ray fluorescence and combustion.

EXAMPLE II

The activity of the silver/nickel catalyst of Example I is demonstrated by oxidative dehydrogenation of ethylbenzene to styrene.

10 Ml. of ethylbenzene was passed over 5 grams of the Ag/Ni catalyst of Example I in a Vycor tube together with air at 300 cc/min. Conditions were: temperature, 260° C; pressure, 1 atmosphere; contact time, 20 seconds. Selectivity to styrene was 73% at 11.7% conversion. Under the same conditions with no catalyst, ethylbenzene was recovered unchanged.

EXAMPLE III

The versatility of the catalyst of Example I is demonstrated by the mild oxidation of p-xylene, i.e., by the oxidation of one methyl group on the benzene ring without affecting the other.

200 Ml. of p-xylene, 1 ml. of tert-butylperoxide and 2 grams of the silver/nickel catalyst of Example I were stirred and refluxed for 24 hours with oxygen at 350 cc/min passing into the liquid. Temperature was 136° C., going to 142° C. after 24 hours. The products were separated by distillation from unreacted p-xylene and analyzed by gas chromatography. A control without the silver/nickel catalyst was run under the same conditions. The product yield of the sample and the control is given in the following:

| Product | Yield-Weight in Grams | |
|---|---|---|
| | Ag/Ni Catalyst | No Ag/Ni Catalyst (Control) |
| p-Toluic Acid | 20.5 | 2.7 |
| p-Methylbenzyl Alcohol | 2.94 | 2.49 |
| p-Methylbenzaldehyde | 3.27 | 1.33 |
| p-Methylbenzyl Toluate | 3.23 | 1.04 |

EXAMPLE IV

The activity of a silver/cobalt catalyst prepared by the inventive process in dehydrogenating ethylbenzene to styrene is demonstrated in the following.

29.1 Grams (0.1 mole) of cobalt nitrate. $6H_2O$ in 200 ml of water were added to 200 ml. of 1 N sodium hydroxide to precipitate cobalt (II) hydroxide. The precipitate was filtered and washed. 16.6 Grams (0.1 mole) of isophthalic acid and 300 ml of water were added to the precipitate. The mixture was stirred and heated at 75° C. for 1½ hours until all solids dissolved. The solution was evaporated to yield 20.0 grams of cobalt (II) isophthalate which analyzed: C, 39.7%; H, 3.0%; Co, 15.0%.

13.5 Grams of silver isophthalate and 1.5 grams of cobalt (II) isophthalate were mixed by being milled together in a solids mill. The mixture analyzed: C, 26.5%; H, 1.3%; Ag, 56.0%; Co, 1.0%. Ten grams of this mixture was calcined at 380° C. under nitrogen for 18 minutes and allowed to cool under nitrogen. The product analyzed: C, 17.9%; H, 0.9%; Ag, 77.0%; Co, 2.0%.

The carbon-like polymer was burned off in air at 150° C. to yield the silver/cobalt catalyst which analysed 98% silver and 2% cobalt.

200 Ml of ethylbenzene, together with air at 300 cc/min., was passed over 5 grams of the silver/cobalt catalyst in a Pyrex tube. Conditions were: temperature, 250° C; 1 atmosphere pressure; contact time, 7.5 seconds. Conversion was 18.3% with selectivity to styrene of 92%.

EXAMPLE V

The coprecipiatation technique was utilized to prepare a silver/vanadium catalyst.

11.7 Grams (0.1 mole) of a solution of ammonium vanadate in 100 ml (0.1 mole) of 1 N sodium hydroxide was blown with air at 70° C. until all ammonia was gone, about 1.5 hours. A solution of 16.6 grams (0.1 mole) of isophthalic acid in 200 ml (0.2 mole) of 1 N sodium hydroxide was added. The resulting solution of sodium metavanadate and sodium isophthalate was added to 150 ml (0.3 mole) of 2N silver nitrate with stirring. The yellow precipitate was collected on a filter, washed and dried. The yield was 53.7 grams of yellow silver isophthalate-silver metavanadate (product I). It decomposed at 330° C. and analyzed 15.9% carbon, 0.6% hydrogen, 50% silver and 8.2% vanadium.

Five grams of the yellow solid were pyrolyzed at 350° C. for ten minutes under nitrogen at 50 cc/min. A carbon-like polymer containing silver and vanadium resulted. It analyzed: C, 10.8%; H, 0.5%; Ag, 61.7%; V, 9.7%. This was designated silver/vanadium catalyst II.

Three grams of II were heated at 200° C. in air at 250 cc/min. for 30 minutes to give a silver/vanadium catalyst III. The analysis of III was: C, 0.08%; H, 0.04%; Ag, 74.5%; V, 11.4%.

EXAMPLE VI

Catalytic activity of catalyst II of Example V was demonstrated by isomerizing 1-pentene.

11.0 Ml (0.1 mole) of 1-pentene in nitrogen was passed over 15 grams of II at 20 cc/min. at 400° C., contact time 23.5 seconds. Conversion was 13% to a mixture of 49% trans-pentene-2, 42% cis-pentene-2, and 9% 2-methyl-butene-2. Under identical conditions with no catalyst 1-pentene was recovered unchanged.

EXAMPLE VII

Catalytic activity of catalyst III of Example V was demonstrated by oxidation of toluene.

10.62 Ml. (0.1 mole) of toluene was passed together with air at 50 cc/min. over 10 grams of catalyst III. Conditions were: temperature, 450° C; contact time, 24.7 seconds. The conversion of toluene to benzaldehyde was 4% with 100% selectivity. Under identical conditions without the catalyst, toluene was recovered unchanged.

EXAMPLE VIII

The coprecipitation technique was utilized to prepare a silver/platinum catalyst.

110 Ml. (0.22 mole) of 2 N silver nitrate was stirred with 600 ml of water. To the mix there was added simultaneously a solution of 5.18 grams (0.01 mole) of chloroplatinic acid in 100 ml of water and a solution of 14.07 grams (0.067 mole) of trimesic acid in 200 ml (0.22 mole) of 1 N sodium hydroxide and 200 ml of water. The white precipitate was collected in a filter, washed, and dried to yield 35.3 grams of product I. The analysis of the product I by combustion and X-ray fluorescence was: C, 19.4%; H, 0.6%; Ag, 57.0%; Pt, 5.7%.

Ten grams of product I were pyrolyzed at 400° C. under nitrogen at 50 cc/min. for ten minutes to give a carbon-like polymer containing silver and platinum, product II. Product II analyzed: C, 12.6%; H, 0.4%; Ag, 67.0%; Pt, 6.8%.

The product II was heated at 200° C. for 40 minutes in air at 250 cc/min. to give catalyst III. Catalyst III analyzed: C, 0.9%; H, 0.04%; Ag, 90.4%; Pt, 8.4%.

EXAMPLE IX

The catalytic activity of catalyst III, as prepared in Example VIII, was demonstrated by the mild oxidation of m-xylene, i.e., by the oxidation of one methyl group on the benzene ring without affecting the other.

150 Ml. of m-xylene and 1 gram of catalyst III of Example VIII were stirred and refluxed for 7 hours with oxygen bubbling through at 500 cc/min. and 1 atmosphere pressure. Temperature was 137° C., going to 140.5° C. after 7 hours. The products were separated by distillation from unreacted m-xylene and analyzed by gas chromatography. A control without the silver/platinum catalyst was run under the same conditions. The product yield of the sample and the control is given in the following:

| Product | Yield-Weight in Grams | |
|---|---|---|
| | Ag/Pt Catalyst | No Ag/Pt Catalyst (Control) |
| m-Methylbenzaldehyde | 2.13 | 0.104 |
| m-Methylbenzyl Alcohol | 3.96 | 0.04 |
| m-Toluic Acid | 3.2 | 0.014 |

EXAMPLE X

A silver/palladium catalyst was prepared by the co-precipitation technique. A solution of 200 ml (0.1 mole) of 0.5 molar sodium isophthalate was added to a stirred mixture of 100 ml (0.2 mole) of 2 N silver nitrate and two grams (0.0087 mole) of palladium nitrate in 300 ml of water. The precipitate was collected on a filter, washed and dried to give silver-palladium isophthalate, product I. Product I analyzed: C, 24.6%; H, 1.3%; Ag, 53.8%; Pd, 2.4%.

Ten grams of product I was pyrolyzed under nitrogen at 50 cc/min. for 10 minutes at 400° C. and allowed to cool under nitrogen, giving a carbon-like polymer containing silver and palladium, catalyst II. Catalyst II analyzed: C, 19.9%; H, 0.7%; Ag, 76.9%; Pd, 3.4%.

Product II was heated at 200° C. in air at 250 cc/min. for 40 minutes to give a silver/palladium catalyst III. Catalyst III analyzed: C, 0.03%; H, 0%; Ag, 94.7%; Pd, 4.1%.

EXAMPLE XI

The catalytic activity of catalyst II of Example X in reducing nitrobenzene with hydrogen was demonstrated in the following. A mixture of 100 ml of nitrobenzene and one gram of catalyst II was stirred and refluxed. Hydrogen at one atmosphere and 500 cc/min. was bubbled through for 2 hours. Conversion was 6%. Selectivity to azobenzene was 91%. The other product was 7% azoxybenzene with traces of aniline and diphenylamine.

EXAMPLE XII

The catalytic activity of catalyst III of Example X in mild oxidation of m-xylene was demonstrated as follows. 150 Ml. of m-xylene was stirred and refluxed with 1 gram of silver/palladium catalyst III for 7 hours. Oxygen was bubbled through the mixture at 500 cc/min. and 1 atmosphere pressure. Temperature was 137° C., going to 140.5° C. after 7 hours. The products were separated by distillation from unreacted m-xylene and analyzed. A control without the silver/palladium catalyst was run under the same conditions. The product yield of the sample and the control is given in the following:

| Product | Yield-Weight in Grams | |
|---|---|---|
| | Ag/Pd Catalyst | No Ag/Pd Catalyst (Control) |
| m-Methylbenzaldehyde | 0.5 | 0.104 |
| m-Methylbenzyl Alcohol | 1.03 | 0.04 |
| m-Toluic Acid | 0.163 | 0.014 |

EXAMPLE XIII

In a procedure similar to that of Example XII, a mixture of 100 ml of p-tert-butyltoluene and one gram of silver/palladium catalyst III of Example X were stirred and refluxed with oxygen for 3 hours at 500 cc/min. and 1 atmosphere pressure. Temperature was 188° C., going to 191° C. after 3 hours. The solution was distilled to recover 84 ml of p-tert butyltoluene at 187°-193° C. The residue was:

2.86 grams p-tert-butylbenzoic acid
2.80 grams p-tert-butylbenzaldehyde
2.28 grams p-tert-butylbenzyl alcohol
3.44 grams p-tert-butylbenzyl-p-tert-butyl benzoate Under identical conditions, a control run without the catalyst gave only unchanged p-tert-butyltoluene.

EXAMPLE XIV

The conditions of Example XIII were repeated except under acid conditions and a lower temperature. A mixture of 50 ml. of p-tert-butyltoluene, 50 ml. of acetic acid and one gram of silver/palladium catalyst III of Example X was stirred and refluxed for 5 hours at 130° C. with oxygen bubbling at 500 cc/min. Conversion was 5% and selectivity 100% to 2-methyl-5-tert-butylphenyl acetic acid. Under identical conditions without the catalyst, the acetic acid and p-tert-butyltoluene were recovered quantitatively.

EXAMPLE XV

The catalytic activity in mild oxidation of 1-methylnaphthalene by catalyst III of Example X was demonstrated. 95 Ml. of 1-methylnaphthalene was mixed with 2 grams of the silver/palladium catalyst III. The mixture was stirred and refluxed for 9.5 hours by bubbling oxygen at 400 cc/min. Temperature was 241° C., rising to 245° C. after 9.5 hours. The products were separated by distillation from unreacted 1-methylnaphthalene. The products consisted of:

3.0 grams 1-naphthaldehyde
0.4 grams 1-naphthylcarbinol
7.7 grams 1-naphthoic acid
5.4 grams 1-naphthylmethyl-1-naphthoate Under identical conditions without catalyst, 1-methylnaphthalene gave a total of 1.4 grams of products not analyzed further.

EXAMPLE XVI

The mild oxidative catalytic ability of catalyst III of Example X on halogen-containing aromatics was exemplified by the oxidation of p-chlorotoluene. A mixture of 100 ml. of p-chlorotoluene and 1 gram of silver/palladium catalyst III was stirred and refluxed for 5.5 hours with oxygen at 500 cc/min. The temperature was 160° C. The products were separated by distillation from unreacted p-chlorotoluene. The products, at 4.3% conversion, were 40% p-chlorobenzaldehyde and 60% p-chlorobenzyl alcohol. Under identical conditions without catalyst, the p-chlorotoluene was recovered unchanged.

EXAMPLE XVII

Catalyst III of Example X mildly oxidizes p-xylene, i.e., it oxidizes one methyl group on the benzene ring without affecting the other.

106 Ml. of p-xylene was mixed with 1 gram of silver/palladium catalyst III. The mixture was stirred and refluxed with oxygen bubbling through for 7 hours at 350 cc/min. Temperature was 136° C. Conversion was 6% to 30.8% of p-methylbenzaldehyde, 38% p-methylbenzyl alcohol and 26% p-toluic acid. Under identical conditions without catalyst, the p-xylene was recovered unchanged.

EXAMPLE XVIII

Cooling under nitrogen decreases the catalytic activity and increases polymer burn-off temperature versus cooling under hydrogen, as shown in the following example.

The silver-nickel isophthalate of Example I was pyrolyzed under nitrogen at 50 cc/min. at 400° C. and allowed to cool to 20° C. under the same flow of nitrogen. Air was admitted at 150 cc/min. The carbon-like polymer did not burn off unitl the temperature was raised to 125° C. The silver/nickel catalyst which remained analyzed: C, 0.5%; H, 0.1%; Ag, 90.1%; Ni, 6.4%.

10 Ml. of ethylbenzene were passed over 5 grams of the Ag/Ni catalyst of this example, Example XVIII, under conditions identical to those of Example II. Selectivity to styrene was 61% at 9.2% conversion. The hydrogen-cooled catalyst of Example II had a selectivity to styrene of 73% at 11.7% conversion.

What is claimed is:

1. A process for dehydrogenating ethylbenzene wherein said ethylbenzene is dehydrogenated at a temperature within the range from about 220° to 300° C in the presence of an oxygen-containing gas and a silver/transition metal catalyst, the transition metal being selected from the group consisting of nickel and cobalt.

2. The process of claim 1 wherein the said ethylbenzene is dehydrogenated to styrene at a temperature within the range from about 220° to 300° C and the said transition metal consists of nickel.

3. The process of claim 1 wherein the said ethylbenzene is dehydrogenated to styrene at a temperature within the range from about 220° to 300° C and the said transition metal consists of cobalt.

* * * * *

UNITED STATES PATENT OFFICE
CERTIFICATE OF CORRECTION

Patent No. 4,069,271   Dated January 17, 1978

Inventor(s) Ellis K. Fields

It is certified that error appears in the above-identified patent and that said Letters Patent are hereby corrected as shown below:

Column 2, line 16 "catalyst activity" should be "catalytic activity"

Column 4, line 49 "hydrogen" should be "hydrogens"

Column 5, line 8 "cyclic or ring" should be "cyclic or ring structure"

Column 7, line 49 "1 1/2 hours" should be "14 hours"

Column 8, line 58 "200 ml" should be "220 ml"

Column 12, line 2 "unitl" should be "until"

Signed and Sealed this

Seventeenth Day of October 1978

[SEAL]

Attest:

RUTH C. MASON
*Attesting Officer*

DONALD W. BANNER
*Commissioner of Patents and Trademarks*